(12) United States Patent
Ichim

(10) Patent No.: US 8,241,621 B2
(45) Date of Patent: Aug. 14, 2012

(54) STEM CELL MEDIATED TREG ACTIVATION/EXPANSION FOR THERAPEUTIC IMMUNE MODULATION

(75) Inventor: Thomas E. Ichim, San Diego, CA (US)

(73) Assignee: Medistem Laboratories, Scottsdale, AZ (US)

( * ) Notice: Subject to any disclaimer, the term of this patent is extended or adjusted under 35 U.S.C. 154(b) by 775 days.

(21) Appl. No.: 11/959,440

(22) Filed: Dec. 18, 2007

(65) Prior Publication Data
US 2008/0159998 A1 Jul. 3, 2008

Related U.S. Application Data

(60) Provisional application No. 60/870,572, filed on Dec. 18, 2006.

(51) Int. Cl.
*C12N 5/071* (2010.01)
*C12N 5/077* (2010.01)
*C12N 5/0783* (2010.01)

(52) U.S. Cl. ............... 424/93.1; 424/93.71; 435/325; 435/372.3; 435/385; 435/386

(58) Field of Classification Search .................. None
See application file for complete search history.

(56) References Cited

U.S. PATENT DOCUMENTS

2006/0292164 A1* 12/2006 Horwitz ............... 424/185.1
2007/0122393 A1* 5/2007 McIntosh et al. ........ 424/93.21
2008/0063652 A1* 3/2008 Pykett et al. ............ 424/184.1

OTHER PUBLICATIONS

Janeway et al. Immunobiology, 2001, Garland Science, Figure A.41.*

* cited by examiner

*Primary Examiner* — Daniel C Gamett
(74) *Attorney, Agent, or Firm* — Baumgartner Patent Law; Marc Baumgartner

(57) ABSTRACT

Disclosed are cells, methods of modulating cells, and therapeutic uses of the cells for the immune modulation of mammals in need thereof. Immune modulation including alteration of cytokine profile, cytotoxic activity, antibody production and inflammatory states is achieved through the administration of various cell types that have been unmanipulated or manipulated in order to endow specific biological activity. Cellular subsets and administration of the subsets in combination with various agents are also provided. One embodiment teaches the previously unknown finding that adipose tissue derived mononuclear cells contain T cells with immune regulatory properties that alone or synergistically with various stem cells induce immune modulation upon administration. Another embodiment is the finding that stimulation of stem cell activation results in stem cell secondary activation of immune modulatory cells, one type which is T regulatory cells (Tregs). One specific embodiment involves extraction of a heterogenous stem cell pool, which contains T regulatory cells, treatment in culture of the population with agents known to stimulate stem cell activation, then subsequent extraction and administration of the purified Tregs. Other embodiments include expansion of Tregs in the presence of antigen in order to generate anti-specific Tregs.

8 Claims, No Drawings

SEQUENCE LISTING

<160> NUMBER OF SEQ ID NOS: 1

<210> SEQ ID NO 1
<211> LENGTH: 17
<212> TYPE: PRT
<213> ORGANISM: Artificial Sequence
<220> FEATURE:
<223> OTHER INFORMATION: Synthetic Construct

<400> SEQUENCE: 1

Cys Asp Asp Tyr Tyr Tyr Gly Phe Gly Cys Asn Lys Phe Cys Arg Pro
1               5                   10                  15

Arg

STEM CELL MEDIATED TREG ACTIVATION/EXPANSION FOR THERAPEUTIC IMMUNE MODULATION

CROSS-REFERENCE TO RELATED APPLICATIONS

This application claims priority under 35 U.S.C. §119 to U.S. Provisional Application Ser. No. 60/870,572 filed Dec. 18, 2006, the entirety of which is hereby incorporated by reference.

FIELD OF THE INVENTION

The current invention pertains to the general area of immune modulation. Specifically, the invention relates to the induction of biological events which are associated with reduction, substantial amelioration of, or complete inhibition of pathological immune responses. More specifically the invention deals with the use of cellular therapies, products of cells, and compounds that are useful for the reprogramming of an immune response.

BACKGROUND OF THE INVENTION

It is widely known that the immune system consists of multicellular interactions that culminate in the inhibition, clearance, and induction of memory to agents that are a threat to the normal functioning of the host. In pathological situations the immune system, or various components thereof, is associated with destruction or impairment of tissue function. These situations are broadly termed "autoimmune diseases" and cause a significant burden on our society. Autoimmune diseases range from Type I diabetes, to multiple sclerosis, to rheumatoid arthritis. Autoimmune processes are also speculated to be implicated in diseases such as atherosclerosis or Amyotrophic lateral sclerosis.

There exists a complex network of mechanisms that focuses the immune system to selectively seek and destroy entities, whether chemical or biological, that are harmful to the host, while at the same time preventing the immune system from attacking the body.

I. Passive Inhibition of Autoreactivity

At a very basic level is the process of thymic selection. T cells, the main effectors of the immune system, develop from bone marrow progenitor sources that undergo a maturation process in the thymus. During T cell maturation, there is approximately $10^{11}$ different types of T cell receptors that are generated. This is due to a process of "gene-shuffling" within developing T cells that causes an incredibly wide variety of T cell specificities to be generated. While the T cells are generated, they are selected for two important features. The first feature is recognition and binding to host MHC, this occurs in positive selection. The second feature is that developing T cells that bind with high affinity to "self" peptides are depleted, this is called "negative selection". Through this mechanism, T cells are generated that can selectively recognize and deal with almost any peptide configuration that is presented to them in the MHC I or MHC II, except those derived from self antigen (since all the T cells recognizing self antigen are negatively selected). It is known that approximately 1% of the T cell progenitors that enter the thymus actually leave as mature T cells, the other 99% are killed either during positive selection or negative selection.

The question naturally arises, as to how the immune system deals with proteins that are expressed after the T cell repertoire is established. For example, during sexual maturity, a wide variety of new proteins start becoming expressed, which were not previously expressed anywhere in the body (at least it was believed) and therefore negative deletion could not have occurred in T cells reactive to those proteins. Polly Matzinger developed a novel way to deal with this problem. She postulated that the immune system does not just recognize "self from non-self" but also, and perhaps more importantly, it makes the decision as to what is "danger" versus "non-danger". This idea is supported by the fact that for the T cells that are generated from the thymus to get activated, they need two signals. The first signal is from the antigen presenting cell, which is in the form of MHC II, or for non-professional antigen presenting cells, MHC I. The second signal is the "costimulatory" signal, which can actually be a wide variety of signals. The most commonly studied costimulatory signal is the CD80/86 on the antigen presenting cell activating the CD28 on the T cell. Numerous other costimulatory signals are known, for example: CD40 ligand, OX40 ligand, and ICOS ligand. The important thing is that activation of T cells by only signal 1, in absence of signal II leads to T cell anergy, apoptosis, or deviation to a T regulatory (Treg) phenotype. The majority of tissues do not express the second signal except during times of inflammation or other tissue damage. Accordingly, T cells that escape the process of thymic deletion, that have autoreactive potential are believed not to cause autoimmunity due to the need for a "danger" signal in order to upregulate expression of the second signal and therefore induce autoimmunity.

The importance of the "Danger" signal is nicely illustrated in experiments in which a foreign antigen is express specifically in the islets. The system is actually transgenic mice containing LCMV protein (foreign antigen) driven by the rat insulin promoter. When these mice are crossed with mice having a transgenic T cell receptor for the LCMV protein, the offspring surprisingly do not develop autoimmunity, despite having circulating autoreactive T cells. However, when the mice are given a "Danger" signal, such as a viral infection, or administration of poly IC, a stimulator of innate immunity, the mice rapidly develop diabetes since the self-tolerance is broken.

However, subsequent to these studies, it was demonstrated that rationale exists for believing that actually all self antigens may be expressed in the thymus, and thereby being important in control of autoreactive T cells. Researchers studying the genetic immune deregulation disease Autoimmune-polyendocrinopathy-candidiasis-ecto-dermaldystrophy identified a gene associated with this disease, whose protein product was found primarily in the thymus [1]. Subsequently it was found that this protein is expressed specifically in thymic medullary epithelial cells and acts as a transcription factor to induce ectopic gene expression. Specifically, the gene, called AIRE (Autoimmune Regulator) was demonstrated to be capable of inducing expression of genes such as insulin, myelin basic protein, and numerous other proteins in the thymus microenvironment [2]. The importance of this process in controlling autoimmunity was demonstrated in that mice lacking AIRE, or having mutant forms of it develop poly-organ autoimmunity [3]. Accordingly, it is currently believed that two main processes associated with passive control of immune responses, these are: first thymic selection and killing of autoreactive T cells in the thymus, and secondly, the need for a second signal in the periphery causes self-reactive T cells to be inactivated when they encounter a self antigen in absence of second signal.

II. Active Inhibition of Autoreactivity: Antigen Presenting Cell Level

In the periphery it is known that T cell activation occurs usually as a result of interaction with dendritic cells (DC), which are one of the only known cells capable of activating naïve T cells. However, the DC are also able to induce active suppression of T cells. For example, lymphoid DC, which are known to possess markers such as the IL-3 receptor CD123, are believed to possess various active T cell suppressive properties. For example, it was demonstrated that pulsing, and subsequent administration of lymphoid DC with the autoantigen myelin basic protein was able to inhibit onset of experimental multiple sclerosis in the rodent EAE model [4]. Additional support for the active immune suppressive role of lymphoid DC comes from experiments demonstrating that the high level of lymphoid DC in murine hepatic allografts is responsible, at least in part, for the low level of rejection seen in this model of transplantation [5, 6]. Interestingly, administration of donor derived hepatic lymphoid DC into murine recipients of islet grafts was able to significantly prolong survival, thus indicating that the tolerogenic properties are not only specific for hepatic tissue, but for donor tissue regardless of histological type [5]. Several mechanisms are known to be responsible for the active induction of T cell inhibition. One is that lymphoid DC express high concentrations of FasL, which is capable of directly killing activated T cells [7]. Another mechanism is that lymphoid DC express high concentrations of T cell suppressive "co-inhibitory" molecules such as OX-2 (CD200) [8, 9]. Indirect inhibition of immune responses through "educating" T cells to express immune suppressive cytokines such as IL-4 and IL-10 has also been reported [10].

In addition to lymphoid DC, immature DC of the myeloid lineage have also been demonstrated to inhibit immune responses. It was reported that ex vivo generation of immature DC through culture in low concentrations of GM-CSF, gave rise to a population of cells expressing low levels of costimulatory molecules and ability to induce donor-specific prolongation of graft survival [11]. In physiological conditions it is believed that immature DC generally are tolerogenic. This was demonstrated in an elegant study in which selective administration of antigen to immature DC was performed through conjugation of the OVA antigen to antibodies binding DEC-205. Since DEC-205 is expressed only on immature, and not mature DC, this system served as a means of assessing whether antigen presentation to immature DC would serve as a mechanism of inducing immunity or tolerance. It was observed that not only did the recipient mice become tolerant to further immunizations with OVA in absence of antibody mediated targeting, but that the mice actually upregulated a population of antigen-specific "suppressor cells" that expressed the CD4+ CD25+ phenotype and could transfer unresponsiveness to naïve mice [12]. This study, and numerous others demonstrated that an active communication, or a "bi-directional loop" occurs between dendritic cells and suppressive T cells in which various types of DC subsets are able to induce antigen-specific enhancement of T cells with suppressive properties, and these T cells are capable of not only suppressing activated T cells, but also causing generation of new immature DC. This was elegantly demonstrated in a model of cardiac tolerance induction [13], as well as reviewed in a paper by the inventor [14].

III. Active Inhibition of Autoreactivity: T Cell Level

In the same manner that conventional T cells are the potent effector side of the immune system, it appears that specific subtypes of T cells called T regulatory cells (Treg), or T suppressor cells, are also the very potent inhibitors of immune activation. The phenomena of "T suppressor" cells was originally described in various systems in the 1970s, in which antigen-specific suppression was claimed by transfer of T cells. Although this work came into disfavor in the 1990s, it is now firmly established that T cells with suppressive activities exist both in human and murine systems. In order to avoid the stigma of the word "suppressor", T cells with suppressive activity are referred to by the majority of immunologists as Treg cells.

The renaissance in Treg research was started in part by experiments showing that mice which where thymectomized neonatally suffered from autoimmunity, and that transfer of T cells with the CD4+ CD25+ phenotype was able to significantly inhibit disease onset [15, 16]. These experiments stimulated numerous groups to demonstrate in numerous systems that cells of the CD4+ CD25+ phenotype possess numerous antigen specific and antigen nonspecific immune regulatory functions. For example, depleting this subset with antibodies accelerates onset of numerous autoimmune disease such as collagen induced arthritis [17], EAE [18], and lymphocyte transfer mediated induction of colitis [19].

The mechanism by which Treg cells suppress other T cells is not entirely known, however, various components that are known include production of TGF-beta by Tregs [20], expression of CTLA4, which induces indolamine 2,3 dioxygenase production in antigen presenting cells, thus rendering them tolerogenic [21], and production of IL-10 [22]. One critical molecule involved in the function of Treg cells is FoxP3, a transcription factor, which when transfected into CD4+ CD25− T cells can not only render them with an active suppressive function, but also endows them with CD25 expression [23].

The clinical importance of Treg cells is apparent in various settings. In oncology, many studies demonstrate association between enhanced Treg function, poor antitumor responses, and shorter survival [24-26]. Accordingly, clinical trials are ongoing to deplete this population in cancer patients, either by using anti-CD25 immunotoxin [27], or by administration of antibodies to CTLA4 [28, 29]. In some clinical trials blocking CTLA4, the immune stimulatory potency of this approach is seen in that some of the patients actual develop an autoimmune like disease [30]. Conversely, in the setting of autoimmunity, numerous autoimmune diseases are associated with suppressed Treg function. For example, rheumatoid arthritis patients have low circulating Treg numbers, however both the number and activity increases in patients responding to anti-TNF therapy [31]. In multiple sclerosis, lower numbers of Tregs are found in the periphery as opposed to controls, and induction of regression is associated with increased Treg number and activity [32]. In ulcerative colitis, an inverse relationship between disease severity index (including endoscopic scores) and numbers of Tregs was reported [33].

IV. Therapeutic Use of TREG Immune Modulation

Despite evidence of success in numerous animal models, then therapeutic use of Treg cells for autoimmunity has been severely limited clinically. Part of the reason for this is the inability to expand large number of antigen-specific Tregs that remain functional for extended periods of time.

Indirectly, Treg therapy is being used in diseases such as Graft Versus Host in which Osiris Therapeutics is administering bone marrow derived mesenchymal cells. It is conceptually possible that these mesenchymal cells are inducing populations of Treg cells in vivo. However, according to U.S.

Pat. No. 6,281,012 held by Osiris Entitled "Method of preparing suppressor T cells with allogeneic mesenchymal stem cells" (incorporated herein by reference in its entirety), the administration of mesenchymal stem cells is restricted to allogeneic mesenchymal stem cells, and the phenotype of the CD8 cell is claimed. The examples demonstrated in the specification seem to teach away from CD4+ CD25+ cell involvement since depletion of the "suppressor cells" with antibodies to CD8 substantially abolished suppressor activity (see, Example 2 from U.S. Pat. No. 6,281,012). Osiris is also currently performing clinical trials with mesenchymal stem cells for patients with Crohn's disease. However no indication of desired generation of Treg cells was made in any of the publications searched. It may be possible that the rationale behind that trial is the harnessing of the tissue regenerative properties of the stem cells.

Other prior art of relevance includes U.S. Patent Application No. 2006/0233751 to Bluestone which teaches the use of Treg cells for treatment of autoimmunity (incorporated by reference in its entirety). The patent provides some means of generating a subpopulation of cells that comprises >98% Treg cells, preferably >98% CD4+, CD25+, CD62L+ Treg cells. According to this application, cells of the desired phenotype are purified using methods known in the art, such as flow cytometry, and subsequently expanded at least 100-fold using antibodies or other ligands to TCR/CD3; CD28, GITR, B7-1/2, CD5, ICOS, OX40 or CD40 and culturing cells in cytokines such as IL-2. This approach has been previously tried in animal models, and although potent expansion is observed, cells eventually lose antigen specificity.

U.S. Patent Application No. 2006/0062763 to Godfrey teaches the extraction of Tregs from cord blood (incorporated by reference in its entirety). The cells are purified from a population of CD45RA+ cord blood cells, wherein the Teg cell suppresses T cell proliferation, the method comprising: a) isolating a population of mononuclear cells from the human umbilical cord blood sample; b) contacting the population of mononuclear cells with an antibody that specifically binds CD25 under conditions suitable for formation of a mononuclear cell-antibody complex; and c) substantially separating the mononuclear cell-antibody complex from the population of mononuclear cells; thereby isolating the Treg cell from a population of phenotypically CD45RA.sup.+ blood cells. Unfortunately, the patent does not disclose methods of expanding these cells ex vivo in an manner to maintain antigen specificity. Additionally, it was well known in the art, prior to September of 2004 (priority date), that CD25 is expressed on Treg cells and that cord blood contains suppressive CD25+ cell populations, which possess a "naïve phenotype" implying CD45RA expression [34].

U.S. Patent Application No. 2006/0115899 to Buckner et al provides methods of ex vivo expansion of Tregs in an antigen specific manner for immunotherapy (incorporated by reference in its entirety). The method claims comprises of selecting CD4+CD25− T cells from a sample obtained from a mammalian subject; determining the MHC Class II type of the subject; inducing the generation of antigen-specific regulatory T cells by contacting the isolated CD4+CD25− T cells in a culture vessel with an induction agent for a time period sufficient to generate antigen-specific CD4+CD25+ regulatory T cells; and selecting the CD4+CD25+ antigen-specific regulatory T cells by sorting the cells in the induction culture with a selection agent comprising at least one artificial multimeric MHC Class II/peptide complex that corresponds to the MHC Class II type of the subject. Unfortunately, this disclosure does not provide enablement over what is in the prior literature, to actually accomplish the goal of generating in large numbers antigen-specific Treg populations.

As seen from the above discussion, there exists great potential for harnessing the therapeutic uses of Treg cells for treatment of inflammatory and autoimmune diseases. Unfortunately, until now, the use of these cells have been hampered by inability to properly expand them, inability to maintain their antigen specificity after expansion, and generally, loss of activity after in vitro or in vivo manipulation.

SUMMARY OF THE INVENTION

Disclosed are cells, methods of modulating cells, and therapeutic uses of the cells for the immune modulation of mammals in need thereof. As used herein, immune modulation may include alteration of cytokine profile, cytotoxic activity, antibody production and inflammatory states is achieved through the administration of various cell types that have been unmanipulated or manipulated in order to endow specific biological activity. Cellular subsets and administration of the subsets in combination with various agents are also provided.

Accordingly, provided herein are methods of immune modulation in a patient comprising the steps of: selecting a patient in need of immune modulation; and administering a therapeutically effective amount of mononuclear cells with enhanced Treg activity. In certain aspects, the mononuclear cells are derived from a source selected from the group consisting of: adipose tissue, bone marrow and cord blood. In certain aspects, the mononuclear cells have been co-cultured with stem cells.

Also provided herein is a method of immune modulating a recipient suffering from a condition associated with an immunological abnormality characterized by Treg deficiency, and/or subfunction, and/or by immunological hyperactivity, so as to ameliorate symptoms or cure the recipient through the steps of: extracting adipose tissue; purifying adipose tissue mononuclear cells; and administering mononuclear cells into the patient. In certain aspects, the adipose derived mononuclear cells are purified from autologous adipose tissue. In certain aspects, the adipose derived mononuclear cells are purified from allogeneic adipose tissue.

In certain aspects, adipose tissue mononuclear cells are maniputaled so as to enhance activity and/or number of Treg through augmenting activity of stem cells within the adipose tissue mononuclear cells.

In certain aspects, the administration of mononuclear cells comprises administration of a cell with a particular phenotype that has been purified so as to possess relative phenotypic homogeneity.

In certain aspects manipulation of adipose tissue mononuclear cells is performed so as to enhance activity and/or number of Treg is performed through activation of stem cells residing within the adipose tissue mononuclear cell fraction.

In certain aspects, activation of the stem cells is performed by culture with a stem cell stimulator.

In certain aspects, the stem cell stimulator is a growth factor, a cytokine, or a small molecule. In certain aspects, the growth factor is selected from a group comprising of: growth hormone, human chorionic gonadotropin, pituitary adenylate cyclase activating polypeptide (PACAP), serotonin, bone morphogenic protein (BMP), epidermal growth factor (EGF), transforming growth factor alpha (TGF.alpha.), fibroblast growth factor (FGF), estrogen, growth hormone, insulin-like growth factor 1, and/or ciliary neurotrophic factor (CNTF), follicle stimulating hormone, prolactin, levothyroxine, L-triiodothyronine, and thyroid stimulating hormone.

In certain aspects, the cytokine is selected from a group comprising of: G-CSF, M-CSF, GM-CSF, IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, kit-L, VEGF, Flt-3 ligand, PDGF, FGF-2, TPO, IL-11, IGF-1, MGDF, NGF, TGF-b, and HMG.

In certain aspects, the small molecule is selected from a group comprising of: thalidomide, 5-azacytidine, trichostatin-A, and valproic acid.

In certain aspects, the activity of the Treg cells within the adipose derived mononuclear cell fraction is increased by culture of the adipose derived mononuclear cells with a concentration of G-CSF and flt3-L sufficient to induce upregulation of Jagged2 on the adipose derived mononuclear cells.

In certain aspects, the culture of mononuclear cells is additionally treated with a concentration of anti-CD3, anti-CD28 and IL-2 to allow expansion of Treg cells.

In certain aspects, the activity of the Treg cells within the adipose derived mononuclear cell fraction is increased by culture of the adipose derived mononuclear cells with a concentration of GM-CSF sufficient to induce upregulation of Jagged2 on the adipose derived mononuclear cells.

In certain aspects, the activity of the Treg cells within the adipose derived mononuclear cell fraction is increased by culture of the adipose derived mononuclear cells with a concentration of TGF-b sufficient to induce upregulation of Jagged2 on the adipose derived mononuclear cells.

In certain aspects, the adipose derived mononuclear cell culture is performed for 2 hours to 100 days.

In certain aspects, the adipose derived mononuclear cell culture is performed for a time period sufficient to induce activation, and/or expansion of Treg cells.

In certain aspects, the activation of Treg cells is observed by ability to suppress an ongoing mixed lymphocyte reaction.

In certain aspects, the expansion of Treg cells is observed by quantification of cells expressing the CD4+ CD25+ phenotype.

In certain aspects, the expansion of Treg cells is observed by quantification of cells expressing the FOXP3+ phenotype.

In certain aspects, the cultured cells having Treg activity are isolated, substantially purified, and administered into a patient, so as to be substantially free of stem cells residing in the culture.

In certain aspects, the cultured cells are administered as a heterogeneous mixture into a recipient in need of therapy.

In certain aspects, the stem cell/Treg cultures are performed in the presence of an antigen to which suppression of immune response is desired in conditions suitable for selective expansion of antigen-specific Treg cells.

In certain aspects, the antigen is selected from a group comprising of: a mixture of autoantigens derived from a patient suffering with autoimmunity, an antigenic peptide, an altered peptide ligand, a recombinant protein, or fragments thereof, and a nucleic acid encoding an antigen.

In certain aspects, the allogeneic adipose derived mononuclear cells are cultured with Tregs isolated from a patient in need of immune modulation, the culture expands Tregs, and HLA-specific Tregs are extracted from the culture and infused into the patient.

Also provided herein is a method of immune modulating a recipient suffering from a condition associated with an immunological abnormality characterized by Treg deficiency, and/or subfunction, and/or by immunological hyperactivity, so as to ameliorate symptoms or cure the recipient through the steps of: extracting bone marrow; purifying bone marrow mononuclear cells; manipulating bone marrow mononuclear cells so as to enhance activity and/or number of Treg; and administering mononuclear cells into the patient.

In certain aspects, the bone marrow mononuclear cells are purified from a bone marrow extraction from an autologous patient.

In certain aspects, the bone marrow mononuclear cells are purified from a bone marrow extraction from an allogeneic patient.

In certain aspects, the manipulation of bone marrow mononuclear cells is performed so as to enhance activity and/or number of Treg through augmenting activity of stem cells within the bone marrow mononuclear cells.

In certain aspects, the administration of mononuclear cells comprises administration of a cell with a particular phenotype that has been purified so as to possess relative phenotypic homogeneity.

In certain aspects, the manipulation of bone marrow mononuclear cells so as to enhance activity and/or number of Treg is performed through activation of stem cells residing within the bone marrow mononuclear cell fraction.

In certain aspects, the activation of the stem cells is performed by culture with a stem cell stimulator.

In certain aspects, the stem cell stimulator is a growth factor, a cytokine, or a small molecule.

In certain aspects, the growth factor is selected from a group comprising of: growth hormone, human chorionic gonadotropin, pituitary adenylate cyclase activating polypeptide (PACAP), serotonin, bone morphogenic protein (BMP), epidermal growth factor (EGF), transforming growth factor alpha (TGF.alpha.), fibroblast growth factor (FGF), estrogen, growth hormone, insulin-like growth factor 1, and/or ciliary neurotrophic factor (CNTF), follicle stimulating hormone, prolactin, levothyroxine, L-triiodothyronine, and thyroid stimulating hormone.

In certain aspects, the cytokine is selected from a group comprising of: G-CSF, M-CSF, GM-CSF, IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, kit-L, VEGF, Flt-3 ligand, PDGF, FGF-2, TPO, IL-11, IGF-1, MGDF, NGF, TGF-b, and HMG.

In certain aspects, the small molecule is selected from a group comprising of: thalidomide, 5-azacytidine, trichostatin-A, and valproic acid.

In certain aspects, the activity of the Treg cells within the bone marrow mononuclear cell fraction is increased by culture of the bone marrow mononuclear cells with a concentration of G-CSF and flt3-L sufficient to induce upregulation of Jagged2 on the bone marrow mononuclear cells.

In certain aspects, the culture of mononuclear cells is additionally treated with a concentration of anti-CD3, anti-CD28 and IL-2 to allow expansion of Treg cells.

In certain aspects, the activity of the Treg cells within the bone marrow mononuclear cell fraction is increased by culture of the bone marrow mononuclear cells with a concentration of GM-CSF sufficient to induce upregulation of Jagged2 on the bone marrow mononuclear cells.

In certain aspects, the activity of the Treg cells within the bone marrow mononuclear cell fraction is increased by culture of the bone marrow mononuclear cells with a concentration of TGF-b sufficient to induce upregulation of Jagged2 on the bone marrow mononuclear cells.

In certain aspects, the bone marrow mononuclear cell culture is performed for 2 hours to 100 days.

In certain aspects, the bone marrow mononuclear cell culture is performed for a time period sufficient to induce activation, and/or expansion of Treg cells.

In certain aspects, the activation of Treg cells is observed by ability to suppress an ongoing mixed lymphocyte reaction.

In certain aspects, the expansion of Treg cells is observed by quantification of cells expressing the CD4+ CD25+ phenotype.

In certain aspects, the expansion of Treg cells is observed by quantification of cells expressing the FOXP3+ phenotype.

In certain aspects, the cultured cells having Treg activity are isolated, substantially purified, and administered into a patient, so as to be substantially free of stem cells residing in the culture.

In certain aspects, the cultured cells are administered as a heterogeneous mixture into a recipient in need of therapy.

In certain aspects, the stem cell/Treg cultures are performed in the presence of an antigen to which suppression of immune response is desired in conditions suitable for selective expansion of antigen-specific Treg cells.

In certain aspects, the antigen is selected from a group comprising of: a mixture of autoantigens derived from a patient suffering with autoimmunity, an antigenic peptide, an altered peptide ligand, a recombinant protein, or fragments thereof, and a nucleic acid encoding an antigen.

In certain aspects, the allogeneic bone marrow mononuclear cell are cultured with Tregs isolated from a patient in need of immune modulation, the culture expands Tregs, and HLA-specific Tregs are extracted from the culture and infused into the patient.

Also provided herein is a method of immune modulating a recipient suffering from a condition associated with an immunological abnormality characterized by Treg deficiency, and/or subfunction, and/or by immunological hyperactivity, so as to ameliorate symptoms or cure the recipient through the steps of: extracting cord blood; purifying cord blood mononuclear cells; manipulating cord blood mononuclear cells so as to enhance activity and/or number of Treg; and administering mononuclear cells into the patient.

In certain aspects, the cord blood mononuclear cells are purified from an autologous patient.

In certain aspects, the cord blood mononuclear cells are purified from an allogeneic patient.

In certain aspects, the manipulation of cord blood mononuclear cells is performed so as to enhance activity and/or number of Treg through augmenting activity of stem cells within the cord blood mononuclear cells.

In certain aspects, the administration of mononuclear cells comprises administration of a cell with a particular phenotype that has been purified so as to possess relative phenotypic homogeneity.

In certain aspects, the manipulation of cord blood mononuclear cells so as to enhance activity and/or number of Treg is performed through activation of stem cells residing within the cord blood mononuclear cells fraction.

In certain aspects, the activation of the stem cells is performed by culture with a stem cell stimulator.

In certain aspects, the stem cell stimulator is a growth factor, a cytokine, or a small molecule.

In certain aspects, the growth factor is selected from a group comprising of: growth hormone, human chorionic gonadotropin, pituitary adenylate cyclase activating polypeptide (PACAP), serotonin, bone morphogenic protein (BMP), epidermal growth factor (EGF), transforming growth factor alpha (TGF.alpha.), fibroblast growth factor (FGF), estrogen, growth hormone, insulin-like growth factor 1, and/or ciliary neurotrophic factor (CNTF), follicle stimulating hormone, prolactin, levothyroxine, L-triiodothyronine, and thyroid stimulating hormone.

In certain aspects, the cytokine is selected from a group comprising of: G-CSF, M-CSF, GM-CSF, IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, kit-L, VEGF, Flt-3 ligand, PDGF, FGF-2, TPO, IL-11, IGF-1, MGDF, NGF, TGF-b, and HMG.

In certain aspects, the small molecule is selected from a group comprising of: thalidomide, 5-azacytidine, trichostatin-A, and valproic acid.

In certain aspects, the activity of the Treg cells within the cord blood mononuclear cell fraction is increased by culture of the cord blood mononuclear cells with a concentration of G-CSF and flt3-L sufficient to induce upregulation of Jagged2 on the cord blood mononuclear cells.

In certain aspects, the culture of mononuclear cells is additionally treated with a concentration of anti-CD3, anti-CD28 and IL-2 to allow expansion of Treg cells.

In certain aspects, the activity of the Treg cells within the cord blood mononuclear cell fraction is increased by culture of the cord blood mononuclear cells with a concentration of GM-CSF sufficient to induce upregulation of Jagged2 on the cord blood mononuclear cells.

In certain aspects, the activity of the Treg cells within the cord blood mononuclear cell fraction is increased by culture of the cord blood mononuclear cells with a concentration of TGF-b sufficient to induce upregulation of Jagged2 on the cord blood mononuclear cells.

In certain aspects, the cord blood mononuclear cell culture is performed for 2 hours to 100 days.

In certain aspects, the cord blood mononuclear cell culture is performed for a time period sufficient to induce activation, and/or expansion of Treg cells.

In certain aspects, the activation of Treg cells is observed by ability to suppress an ongoing mixed lymphocyte reaction.

In certain aspects, the expansion of Treg cells is observed by quantification of cells expressing the CD4+ CD25+ phenotype.

In certain aspects, the expansion of Treg cells is observed by quantification of cells expressing the FOXP3+ phenotype.

In certain aspects, the cultured cells having Treg activity are isolated, substantially purified, and administered into a patient, so as to be substantially free of stem cells residing in the culture.

In certain aspects, the cultured cells are administered as a heterogeneous mixture into a recipient in need of therapy.

In certain aspects, the stem cell/Treg cultures are performed in the presence of an antigen to which suppression of immune response is desired in conditions suitable for selective expansion of antigen-specific Treg cells.

In certain aspects, the antigen is selected from a group comprising of: a mixture of autoantigens derived from a patient suffering with autoimmunity, an antigenic peptide, an altered peptide ligand, a recombinant protein, or fragments thereof, and a nucleic acid encoding an antigen.

In certain aspects, allogeneic cord blood mononuclear cells are cultured with Tregs isolated from a patient in need of immune modulation, the culture expands Tregs, and HLA-specific Tregs are extracted from the culture and infused into the patient.

In certain aspects, an inhibitor of an inhibitor of FOXP3 is added to culture of stem cells/Treg in order to potentiate the activation of Tregs. In certain aspects, the inhibitor blocks activation of signaling pathways selected from a group comprising of: NF-kB, mTOR, and PI3-kinase. In certain aspects, the inhibitor is an antibody to cytokines selected from a group comprising of: TNF-alpha, TNF-beta, IL-1, IL-6, IL8, IL12, IL15, IL17, IL-18, IL21, IL23, IL27, and IFN-gamma. In certain aspects, the inhibitor is rapamycin. In certain aspects, the inhibitor is wortmannin.

In certain aspects, Treg activation implies endowment of Treg activity on a cell that previously was not considered a Treg. In certain aspects, the cell previously not considered a Treg lacked ability to suppress a mixed lymphocyte reaction. In certain aspects, the cell previously not considered a Treg lacked ability to suppress a cytotoxic T cell response. In certain aspects, the cell previously not considered a Treg lacked ability to inhibit DC maturation. In certain aspects, the cell previously not considered a Treg lacked ability to inhibit T cell production of inflammatory cytokines.

Also provided herein is a method of treating an autoimmune disease in a mammal comprising the steps of: collecting a population of stem cells; culturing the stem cells with lymphocytes; and administration of cultured lymphocytes into the mammal.

In certain aspects, the stem cells consist of cells selected from a group comprising of stem cells, committed progenitor cells, and differentiated cells.

In certain aspects, the stem cells are selected from a group comprising of: embryonic stem cells, cord blood stem cells, placental stem cells, bone marrow stem cells, amniotic fluid stem cells, neuronal stem cells, circulating peripheral blood stem cells, mesenchymal stem cells, germinal stem cells, adipose tissue derived stem cells, exfoliated teeth derived stem cells, hair follicle stem cells, dermal stem cells, parthenogenically derived stem cells, reprogrammed stem cells and side population stem cells.

In certain aspects, the embryonic stem cells are totipotent.

In certain aspects, the embryonic stem cells express one or more antigens selected from a group consisting of: stage-specific embryonic antigens (SSEA) 3, SSEA 4, Tra-1-60 and Tra-1-81, Oct-3/4, Cripto, gastrin-releasing peptide (GRP) receptor, podocalyxin-like protein (PODXL), Rex-1, GCTM-2, Nanog, and human telomerase reverse transcriptase (hTERT).

In certain aspects, the cord blood stem cells are multipotent and capable of differentiating into endothelial, muscle, and neuronal cells.

In certain aspects, the cord blood stem cells are identified based on expression of one or more antigens selected from a group comprising: SSEA-3, SSEA-4, CD9, CD34, c-kit, OCT-4, Nanog, and CXCR-4

In certain aspects, the cord blood stem cells are unrestricted somatic stem cells.

In certain aspects, the cord blood stem cells do not express one or more markers selected from a group comprising of: CD3, CD45, and CD11b.

In certain aspects, the placental stem cells are isolated from the placental structure.

In certain aspects, the placental stem cells are identified based on expression of one or more antigens selected from a group comprising: Oct-4, Rex-1, CD9, CD13, CD29, CD44, CD166, CD90, CD105, SH-3, SH-4, TRA-1-60, TRA-1-81, SSEA-4 and Sox-2.

In certain aspects, the bone marrow stem cells comprise of bone marrow mononuclear cells.

In certain aspects, the bone marrow stem cells are selected based on the ability to differentiate into one or more of the following cell types: endothelial cells, muscle cells, and neuronal cells.

In certain aspects, the bone marrow stem cells are selected based on expression of one or more of the following antigens: CD34, c-kit, flk-1, Stro-1, CD105, CD73, CD31, CD146, vascular endothelial-cadherin, CD133 and CXCR-4.

In certain aspects, the bone marrow stem cells are enriched for expression of CD133.

In certain aspects, the amniotic fluid stem cells are isolated by introduction of a fluid extraction means into the amniotic cavity under ultrasound guidance.

In certain aspects, the amniotic fluid stem cells are selected based on expression of one or more of the following antigens: SSEA3, SSEA4, Tra-1-60, Tra-1-81, Tra-2-54, HLA class I, CD13, CD44, CD49b, CD105, Oct-4, Rex-1, DAZL and Runx-1.

In certain aspects, the amniotic fluid stem cells are selected based on lack of expression of one or more of the following antigens: CD34, CD45, and HLA Class II.

In certain aspects, the neuronal stem cells are selected based on expression of one or more of the following antigens: RC-2, 3CB2, BLB, Sox-2hh, GLAST, Pax 6, nestin, Muashi-1, NCAM, A2B5 and prominin.

In certain aspects, the circulating peripheral blood stem cells are characterized by the ability to proliferate in vitro for a period of over 3 months.

In certain aspects, the circulating peripheral blood stem cells are characterized by expression of CD34, CXCR4, CD117, CD113, and c-met.

In certain aspects, the circulating peripheral blood stem cells lack substantial expression of differentiation associated markers.

In certain aspects, the differentiation associated markers are selected from a group comprising of CD2, CD3, CD4, CD11, CD11a, Mac-1, CD14, CD16, CD19, CD24, CD33, CD36, CD38, CD45, CD56, CD64, CD68, CD86, CD66b, and HLA-DR.

In certain aspects, the mesenchymal stem cells express one or more of the following markers: STRO-1, CD105, CD54, CD106, HLA-I markers, vimentin, ASMA, collagen-1, fibronectin, LFA-3, ICAM-1, PECAM-1, P-selectin, L-selectin, CD49b/CD29, CD49c/CD29, CD49d/CD29, CD61, CD18, CD29, thrombomodulin, telomerase, CD10, CD13, STRO-2, VCAM-1, CD146, and THY-1.

In certain aspects, the mesenchymal stem cells do not express substantial levels of HLA-DR, CD117, and CD45.

In certain aspects, the mesenchymal stem cells are derived from a group selected of: bone marrow, adipose tissue, umbilical cord blood, placental tissue, peripheral blood mononuclear cells, differentiated embryonic stem cells, and differentiated progenitor cells.

In certain aspects, the germinal stem cells express markers selected from a group comprising of: Oct4, Nanog, Dppa5 Rbm, cyclin A2, Tex18, Stra8, Dazl, beta1- and alpha6-integrins, Vasa, Fragilis, Nobox, c-Kit, Sca-1 and Rex1.

In certain aspects, the adipose tissue derived stem cells express markers selected from a group comprising of: CD13, CD29, CD44, CD63, CD73, CD90, CD166, Aldehyde dehydrogenase (ALDH), and ABCG2.

In certain aspects, the adipose tissue derived stem cells are a population of purified mononuclear cells extracted from adipose tissue capable of proliferating in culture for more than 1 month.

In certain aspects, the exfoliated teeth derived stem cells express markers selected from a group comprising of: STRO-1, CD146 (MUC18), alkaline phosphatase, MEPE, and bFGF.

In certain aspects, the hair follicle stem cells express markers selected from a group comprising of: cytokeratin 15, Nanog, and Oct-4.

In certain aspects, the hair follicle stem cells are capable of proliferating in culture for a period of at least one month.

In certain aspects, the hair follicle stem cells secrete one or more of the following proteins when grown in culture: basic fibroblast growth factor (bFGF), endothelin-1 (ET-1) and stem cell factor (SCF).

In certain aspects, the dermal stem cells express markers selected from a group comprising of: CD44, CD13, CD29, CD90, and CD105.

In certain aspects, the dermal stem cells are capable of proliferating in culture for a period of at least one month.

In certain aspects, the parthenogenically derived stem cells are generated by addition of a calcium flux inducing agent to activate an oocyte followed by enrichment of cells expressing markers selected from a group comprising of SSEA-4, TRA 1-60 and TRA 1-81.

In certain aspects, the reprogrammed stem cells are selected from a group comprising of: cells subsequent to a nuclear transfer, cells subsequent to a cytoplasmic transfer, cells treated with a DNA methyltransferase inhibitor, cells treated with a histone deacetylase inhibitor, cells treated with a GSK-3 inhibitor, cells induced to dedifferentiate by alteration of extracellular conditions, and cells treated with various combination of the mentioned treatment conditions.

In certain aspects, the nuclear transfer comprises introducing nuclear material to a cell substantially enucleated, the nuclear material deriving from a host whose genetic profile is sought to be dedifferentiated.

In certain aspects, the cytoplasmic transfer comprises introducing cytoplasm of a cell with a dedifferentiated phenotype into a cell with a differentiated phenotype, such that the cell with a differentiated phenotype substantially reverts to a dedifferentiated phenotype.

In certain aspects, the DNA demethylating agent is selected from a group comprising of: 5-azacytidine, psammaplin A, and zebularine.

In certain aspects, the histone deacetylase inhibitor is selected from a group comprising of: valproic acid, trichostatin-A, trapoxin A and depsipeptide.

In certain aspects, the side population cells are identified based on expression multidrug resistance transport protein (ABCG2) or ability to efflux intracellular dyes such as rhodamine-123 and or Hoechst 33342.

In certain aspects, the side population cells are derived from tissues such as pancreatic tissue, liver tissue, muscle tissue, striated muscle tissue, cardiac muscle tissue, bone tissue, bone marrow tissue, bone spongy tissue, cartilage tissue, liver tissue, pancreas tissue, pancreatic ductal tissue, spleen tissue, thymus tissue, Peyer's patch tissue, lymph nodes tissue, thyroid tissue, epidermis tissue, dermis tissue, subcutaneous tissue, heart tissue, lung tissue, vascular tissue, endothelial tissue, blood cells, bladder tissue, kidney tissue, digestive tract tissue, esophagus tissue, stomach tissue, small intestine tissue, large intestine tissue, adipose tissue, uterus tissue, eye tissue, lung tissue, testicular tissue, ovarian tissue, prostate tissue, connective tissue, endocrine tissue, and mesentery tissue.

In certain aspects, the committed progenitor cells are selected from a group comprising of: endothelial progenitor cells, neuronal progenitor cells, and hematopoietic progenitor cells.

In certain aspects, the committed endothelial progenitor cells are purified from the bone marrow.

In certain aspects, the committed endothelial progenitor cells are purified from peripheral blood.

In certain aspects, the committed endothelial progenitor cells are purified from peripheral blood of a patient whose committed endothelial progenitor cells are mobilized by administration of a mobilizing agent or therapy.

In certain aspects, the mobilizing agent is selected from a group comprising of: G-CSF, M-CSF, GM-CSF, 5-FU, IL-1, IL-3, kit-L, VEGF, Flt-3 ligand, PDGF, EGF, FGF-1, FGF-2, TPO, IL-11, IGF-1, MGDF, NGF, HMG CoA) reductase inhibitors and small molecule antagonists of SDF-1.

In certain aspects, the mobilization therapy is selected from a group comprising of: exercise, hyperbaric oxygen, autohemotherapy by ex vivo ozonation of peripheral blood, and induction of SDF-1 secretion in an anatomical area outside of the bone marrow.

In certain aspects, the committed endothelial progenitor cells express markers selected from a group comprising of: CD31, CD34, AC133, CD146 and flk1.

In certain aspects, the committed hematopoietic cells are purified from the bone marrow.

In certain aspects, the committed hematopoietic progenitor cells are purified from peripheral blood.

In certain aspects, the committed hematopoietic progenitor cells are purified from peripheral blood of a patient whose committed hematopoietic progenitor cells are mobilized by administration of a mobilizing agent or therapy.

In certain aspects, the mobilizing agent is selected from a group comprising of: G-CSF, M-CSF, GM-CSF, 5-FU, IL-1, IL-3, kit-L, VEGF, Flt-3 ligand, PDGF, EGF, FGF-1, FGF-2, TPO, IL-11, IGF-1, MGDF, NGF, HMG CoA) reductase inhibitors and small molecule antagonists of SDF-1.

In certain aspects, the mobilization therapy is selected from a group comprising of: exercise, hyperbaric oxygen, autohemotherapy by ex vivo ozonation of peripheral blood, and induction of SDF-1 secretion in an anatomical area outside of the bone marrow.

In certain aspects, the mobilization therapy is induction of SDF-1 secretion in an anatomical area outside of the bone marrow.

In certain aspects, the committed hematopoietic progenitor cells express the marker CD133.

In certain aspects, the committed hematopoietic progenitor cells express the marker CD34.

In certain aspects, the culture is performed under conditions conducive for generation, and/or expansion, and/or activation of Treg cells from lymphocytes.

In certain aspects, the Treg cells are capable of suppressing a mixed lymphocyte reaction.

In certain aspects, the Treg cells are capable of inhibiting inflammatory cytokine production for other T cells.

In certain aspects, the Treg cells are capable of inhibiting inflammatory cytotoxicity of other T cells.

In certain aspects, the Treg cells are capable of inhibiting DC maturation.

In certain aspects, the culture conditions conducive for Treg generation, and/or expansion, and/or activation consist of one or more steps from the following:
 a) coculture of lymphocytes with activated stem cells
 b) addition of one or more T cell stimulators to the culture
 c) addition of one or more stimulators of Treg generation
 d) addition of an inhibitor of pathways inhibitory for Treg generation; and
 e) addition of a cell type that is stimulatory for Treg generation.

In certain aspects, the lymphocytes are selected from a group comprising of: unfractionated lymphocytes derived from an anatomical location known to possess stem cell activity, T cells, Treg cells, Helper T-cells, NK cells, NKT cells, gamma delta T cells, T cells generated by transdifferentiation, and T cells generated from embryonic stem cell sources.

In certain aspects, the lymphocytes are CD4+ CD25+ Treg.

In certain aspects, the T cell is either a heterogeneous population of T cells, or T cells purified for expression of either Th1, Th2, Th3, or Th17 profiles.

In certain aspects, the T cell is suppressive to other immune cells.

In certain aspects, the suppressive T cell expresses TGF-b on its membrane.

In certain aspects, the stem cells are activated through culture with a stem cell stimulator.

In certain aspects, the stem cell stimulator is a growth factor, a cytokine, or a small molecule.

In certain aspects, the growth factor is selected from a group comprising of: growth hormone, human chorionic gonadotropin, pituitary adenylate cyclase activating polypeptide (PACAP), serotonin, bone morphogenic protein (BMP), epidermal growth factor (EGF), transforming growth factor alpha (TGF.alpha.), fibroblast growth factor (FGF), estrogen, growth hormone, insulin-like growth factor 1, and/or ciliary neurotrophic factor (CNTF), follicle stimulating hormone, prolactin, levothyroxine, L-triiodothyronine, and thyroid stimulating hormone.

In certain aspects, the cytokine is selected from a group comprising of: G-CSF, M-CSF, GM-CSF, IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, kit-L, VEGF, Flt-3 ligand, PDGF, FGF-2, TPO, IL-11, IGF-1, MGDF, NGF, TGF-b, and HMG.

In certain aspects, the small molecule is selected from a group comprising of: thalidomide, 5-azacytidine, trichostatin-A, valproic acid, and small molecule stimulators of the Notch pathway, such as the DSL peptide.

In certain aspects, the stimulator of Treg generation is chosen from a group comprising of: anti-CD3, anti-CD28, CTLA4-IG, IL-2, IL-4, IL-7, TSLP, and TGF-b.

In certain aspects, the inhibitors of pathways inhibitory for Treg generation are selected from a group comprising of inhibitors of the: NF-kB, mTOR, and PI3-kinase signal transduction pathways.

In certain aspects, the inhibitor is an antibody to cytokines selected from a group comprising of: TNF-alpha, TNF-beta, IL-1, IL-6, IL8, IL12, IL15, IL17, IL-18, IL21, IL23, IL27, and IFN-gamma.

In certain aspects, the inhibitor is rapamycin.

In certain aspects, the inhibitor is wortmannin.

In certain aspects, the cell type stimulatory for Treg generation is a suppressive dendritic cell.

In certain aspects, the suppressive dendritic cell is of the lymphoid lineage.

In certain aspects, the suppressive dendritic cell is of the myeloid lineage and is in a state of immaturity.

In certain aspects, the dendritic cell of the myeloid lineage and in a state of immaturity expresses low levels of molecules selected from a group comprising of: MHC II, CD80, CD86, CD154, and IKK.

In certain aspects, the dendritic cell of the myeloid lineage and in a state of immaturity is generated by culture in low concentrations of GM-CSF in absence of IL-4.

In certain aspects, the dendritic cell of the myeloid lineage and in a state of immaturity is generated by culture in IL-10.

In certain aspects, the dendritic cell of the myeloid lineage and in a state of immaturity is generated by culture in TGF-b.

In certain aspects, the dendritic cell of the myeloid lineage and in a state of immaturity is generated by culture in the presence of inhibitors of NF-kB.

In certain aspects, the inhibitors of NF-kB are selected from a group comprising of: rapamycin, LF-15095, salicylic acid, siRNA specific to NF-kB subunits, and decoy oligonucleotides which inhibit NF-kB DNA binding.

In certain aspects, the cell stimulatory for Treg generation is a cell genetically engineered to express proteins selected from a group comprising of: Jagged2, TGF-b, IL-10, and IL-20.

In certain aspects, subsequent to administration of Treg, or Treg/stem cell combinations to a patient in need of immune modulation, the patient is subsequently treated with agents known to increase Treg activity and/or expansion.

In certain aspects, the agents known to increase Treg activity and/or expansion are selected from a group comprising of: antibodies to TNF-alpha, TNF-beta, IL-1, IL-6, IL8, IL12, IL15, IL17, IL-18, IL21, IL23, IL27, and IFN-gamma; rapamycin; and anti-inflammatory agents.

DETAILED DESCRIPTION OF THE PREFERRED EMBODIMENT

The current invention teaches that Treg cells can be endowed with enhanced functional immune suppressive activity, as well as in some cases be induced to proliferate through coculture with stem cells.

One of the principle teachings of the current invention is that Treg cells serve as a "negative feedback regulator" to stem cell proliferation. Accordingly, activation of stem cell proliferation induces expression of various signals on the stem cells, the signals serving to activate Treg cells to inhibit the stem cells. The invention capitalizes on the fact that Tregs can be copurified with stem cells, and the Tregs possess higher suppressive activity as compared to Tregs from peripheral blood. Furthermore, the invention takes advantage of the fact that stem cell activation by cytokines induces enhanced Treg activity that not only inhibits the stem cell, but inhibits other immunological cells. Accordingly, one aspect of the invention is the activation of stem cells so as to cause enhanced Treg activity, the Treg activity being therapeutically useful for treatment of diseases that are known to benefit from the enhanced Treg activity.

In one aspect stem cells are derived from autologous sources such as bone marrow, adipose tissue, or peripheral blood. Stem cells are either co-purified with endogenous Tregs or Tregs are added to the stem cells in vitro. In a specific aspect, the stem cell/Treg mixture is administered without manipulation into a patient suffering from a disorder associated with immune abnormality, such as an autoimmune disorder. Stem cell/Treg mixtures are administered at sufficient frequency to induce amelioration or substantial cure of the disorder.

In another aspect of the invention, stem cells are endowed a phenotype that is conducive for Treg activation and/or expansion. The phenotype may be endowed through activation of stem cells to proliferate and/or differentiate. Specifically, stem cells may be activated with cytokines, growth factors, culture on various extracellular matrices, or culture under conditions known to activate stem cells such as hypoxia. The stem cells may initially isolated, activated, and subsequently cultured with Tregs, or conversely the stem cells may be activated while cocultured with Tregs.

In some aspects, stem cells are cultured with cells that do not have the Treg phenotype, for example, expression of FoxP3, but subsequent to culture, the cells acquire Treg phenotype.

In a particular aspect of the invention, adipose tissue derived mononuclear cells are isolated and administered into a patient with an immunological disorder so as to cause amelioration or cure of such disorder. The cells may be administered directly after purification, or may be cultured in various conditions so as to enhance stem cell activation, and in turn enhance Treg activation.

In a particular aspect of the invention, bone marrow derived mononuclear cells are isolated and administered into a patient with an immunological disorder so as to cause amelioration or cure of such disorder. The cells may be administered directly after purification, or may be cultured in various conditions so as to enhance stem cell activation, and in turn enhance Treg activation.

In a particular aspect of the invention, cord blood derived mononuclear cells are isolated and administered into a patient with an immunological disorder so as to cause amelioration or cure of such disorder. The cells may be administered directly after purification, or may be cultured in various conditions so as to enhance stem cell activation, and in turn enhance Treg activation.

In another aspect, agents are added to the stem cell/Treg populations so as to enhance Treg activation in addition to the activation signals obtained from the stem cells. Treg activation signals may be provided by various means such as culture with antibodies, chemical stimulators of Treg function, and inhibitors of Treg inhibition.

In another aspect the stem cell/Treg populations are cultured so as to allow for expansion of autologous Treg cells. Expansion of autologous Treg cells residing in the adipose mononuclear cell fraction extracted from tissues known to contain stem cells is performed, according to the current invention, by activation of the stem cell compartment, which in turn, activates the Treg activity. Specific means of activation include co-culture with growth factors, cytokines, extracellular matrices, and various other conditions known in the art to induce stem cell proliferation. Ways of assessing level of Treg activity during culture including extracting aliquot samples from the culture and assessing ability of purified CD4+ CD25+ cells from the culture to suppress proliferation of CD4+ CD25− cells. Alternative means of assessing the suppressive activity could include quantification of FOXP3 expression in the cells by means such as flow cytometry.

In another aspect, stem cell/Treg mixtures are administered into a patient, and the patient is treated with immune modulators so as to expand Treg numbers and activities.

In another aspect, stem cell/Treg mixtures are cultured together with an antigen so as to induce selective expansion of antigen specific Treg cells. In this aspect, the antigen may be an autoantigen, an epitope of an autoantigen, or a polyepitope mixture. Specifically, the autoantigen may be synthetically generated, for example as a peptide or recombinant protein, or may be a biological mixture extracted from the patient, such as gut luminal antigens extracted by endoscopic biopsy in patients with inflammatory bowel disease.

In one aspect the invention provides the generation of an immune modulatory cell preparation with tolerogenic aspects, the preparation comprising of adipose derived mononuclear cells that have been cultured in vitro for a period of 1-5 days in the presence of an inhibitor of the mammalian target of rapamycin (mTOR). The cells are cultured for a sufficient time point and at a sufficient concentration of the mTOR inhibitor so as to allow upregulation of suppressive properties of the cells.

In another aspect, adipose derived mononuclear cells are extracted from a patient with an inflammatory condition, and culture of the mononuclear cells is performed so as to allow for expansion for Tregs. The culture may include administration of plate bound anti-CD3 antibodies, IL-2, TGF, and other factors known to selectively expand Treg cells. Addition of stem cell stimulators may be performed but is optional. Subsequently, cells from the culture are extracted and assessed for immune suppressive potential. If desirable, antigen specific T cells may be generated by coculture with the antigen of interest. Antigen specificity may subsequently be assessed using various means known in the art, such as suppression of antigen specific T cell proliferation, cytokine release, or cytotoxic function.

In another aspect, Tregs are generated, and/or expanded, and/or activity through various means by coculture with stem cells, and the Treg cells are purified out of the culture and administered into a patient in need of therapy.

In another aspect, Treg generation from non-Treg cells is mediated by culture of the non-Treg cells with a stimulus of proliferation, such as anti-CD3, while in order to compensate for absence of CD28 costimulation, a stem cell is added as a "costimulator" which provides a survival signal, so as to allow for the differentiation and survival of a non-Treg cell into a Treg.

In another aspect, a population of dendritic cells with tolerogenic capabilities is expanded and cultured in combination with a Treg population and a stem cell population so as to allow for activation, enhanced suppressive properties, and proliferation of the Treg cell.

In another aspect, a method of screening agents for ability to endow stem cells with Treg generating capability is disclosed. The method of screening comprising of:
a) Culturing a population of T cells and stem cells;
b) Administration of the agent to be screened into the population of T cells and stem cells; and
c) Assessment of FOXP3 in the coculture.

In another aspect, a method of screening agents for ability to endow stem cells with Treg generating capability is disclosed. The method of screening comprising of:
a) Obtaining a stem cell population;
b) Culturing the stem cell population with the agent being screened; and
c) Assessing expression of notch ligands on the stem cells harvested from the culture. Various notch ligands are known in the art. One particular one useful for the practice of the current invention is Jagged2. Expression of Jagged2 may be determined by immunological or molecular means.

In another aspect of the invention, Treg cells are purified from a mononuclear preparation of a tissue associated with stem cell anatomical niches and subsequently administered into a patient in need of therapy. The anatomical niches include bone marrow, cord blood, mobilized peripheral blood, and adipose tissue.

In another aspect of the invention, stem cell/Treg cultures are treated with an activator of the notch signaling pathway, or an inhibitor of an inhibitor of a notch signaling pathway. This may be performed alongside stem cell and/or Treg stimulation. In one specific aspect, the stem cell/Treg culture is treated with the DSL peptide CDDYYYGFGCNKFCRPR (SEQ ID NO: 1) or analogues thereof.

In one aspect of the invention, the use of unmanipulated adipose derived mononuclear cells for immune modulation is disclosed. It is known that adipose tissue contains numerous stem cell populations. For example, culture of adipose derived mononuclear cells in TGF-b is causes them to differentiate into chondrocytes [35]. The same is true for culture of these cells in bone morphogenic protein-2 [36]. Additionally, adipose tissue derived cells can differentiation into smooth muscle cells after treatment with sphingosylphosphorylcholine [37] or other agents [38]. Various culture conditions, as well as in vivo experiments have demonstrate ability of adipose derived cells to differentiate into skeletal muscle, including in the animal model of muscular dystrophy (mdx) [39, 40]. Culture of these cells in HGF, bFGF and nicotinamide for 14 days can lead to generation of hepatic-like cells that express albumin and several other liver-specific genes in addition to attaining a cuboidal, hepatocyte-like appearance [41]. In fact, it is reported that adipose derived stem cells have a similar hepatogenic differentiation potential to bone marrow derived stem cells, but are able to be cultured in vitro for a longer period and possess a higher proliferation capacity, as well as are able to generate albumin in vivo [42, 43]. Like bone marrow cells, they also can be induced to differentiate into endothelium [44]. Given the mentioned stem cell properties of adipose derived mononuclear cells, we see these as one of the preferred stem cell types for use in the context of the current invention.

In one embodiment, the invention is used for generation of an autologous preparation of cells that contains immune modulatory properties and is useful for the treatment of inflammatory diseases such as autoimmunity. Specifically, adipose tissue mononuclear cells are harvested from an autologous donor suffering from an autoimmune disease. Harvesting techniques are well known in the art and starting material can be obtained with relative ease during standard liposuction procedures. In one specific embodiment, adipose tissue fragments are collected and digested with collagenase I at a final concentration of approximately 1 mg/mL) in Hanks Buffered Saline at 37 Celsius for approximately 60 min with intermittent shaking. Thereafter, the resulting suspensions are filtered using two layers of cotton gauze to remove debris and then centrifuged at 400 g for 10 min. Other methods are known in the art for preparation of mononuclear cells from adipose tissue [45, 46]. In this particular method, supernatants are discarded and pellets are resuspended in 160 mmol/L NH4Cl at room temperature for 10 min to lyse the remaining red blood cells. Cells are collected by centrifugation, resuspended in culture medium (DMEM-low glucose supplemented with 15% autologous serum and 50 mg/mL of gentamicine). In order to generate a Treg population in a short amount of time, the cytokine G-CSF is administered to the cell culture in vitro at a concentration of about 0.1-500 ng/ml G-CSF. Cells are subsequently cultured in tissue culture flasks in a humidified atmosphere at 37 Celsius with 50 mL/L CO2 for about 2 h to 100 days. Cells are continually provided fresh media. In some embodiments other growth factors may be added, for example, Flt3L may be added at a concentration of about 0.1-500 ng/ml, IL-3 may be added at a concentration of about 0.1-700 ng/ml IL-3, and GM-CSF may be added at a concentration of about 0.1-500 ng/ml. Treg activity may be measured by taking aliquots of cells from the culture and measuring their ability to inhibit mixed lymphocyte reaction and cytokine production as previously described by the inventor [13]. Additional agents may be introduced into the culture to provide ideal conditions for Treg expansion, these include inhibitors of NF-kB, and/or mTOR, and/or P13-kinase.

The inhibitors may be one or several antibodies to cytokines selected from a group comprising of: TNF-alpha, TNF-beta, IL-1, IL-6, IL8, IL12, IL15, IL17, IL-18, IL21, IL23, IL27, and IFN-gamma. Inhibitors of mTOR may include rapamycin, and inhibitors of PI3K may include wortmannin.

Cells are subsequently re-injected into the patient suffering from a disorder in need of immune modulation. Medical conditions in which treatment with the invention disclosed may be useful include: Thyroiditis, insulitis, multiple sclerosis, iridocyclitis, uveitis, orchitis, hepatitis, Addison's disease, myasthenia gravis, rheumatoid arthritis, lupus erythematosus, immune hyperreactivity, insulin dependent diabetes mellitus, anemia (aplastic, hemolytic), autoimmune hepatitis, skleritis, idiopathic thrombocytopenic purpura, inflammatory bowel diseases (Crohn's disease, ulcerative colitis), juvenile arthritis, scleroderma and systemic sclerosis, sjogren's syndrom, undifferentiated connective tissue syndrome, antiphospholipid syndrome, vasculitis (polyarteritis nodosa, allergic granulomatosis and angiitis, Wegner's granulomatosis, Kawasaki disease, hypersensitivity vasculitis, Henoch-Schoenlein purpura, Behcet's Syndrome, Takayasu arteritis, Giant cell arteritis, Thrombangiitis obliterans), polymyalgia rheumatica, essentiell (mixed) cryoglobulinemia, Psoriasis vulgaris and psoriatic arthritis, diffus fasciitis with or without eosinophilia, polymyositis and other idiopathic inflammatory myopathies, relapsing panniculitis, relapsing polychondritis, lymphomatoid granulomatosis, erythema nodosum, ankylosing spondylitis, Reiter's syndrome, inflammatory dermatitis, unwanted immune reactions and inflammation associated with arthritis, including rheumatoid arthritis, inflammation associated with hypersensitivity and allergic reactions, systemic lupus erythematosus, collagen diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of strokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery or organ, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

EXAMPLES

Treatment of Ulcerative Colitis with Autologous Adipose Mononuclear Cell Therapy Trial Design: A double blind, randomized study aimed at determining efficacy of adipose derived, stem cell activated Treg is performed. A population of 110 patients is enrolled and randomized into either the placebo or treatment group. Eligible patients are assessed for baseline (pre-treatment) clinical values and treated with daily placebo cell therapy administration, or adipose derived, rapamycin activated Treg. Patients are allowed to continue taking current treatment, however medical need for escalation of current (non experimental) treatment leads to exclusion of the patient from the study. Effect evaluation occurs at Weeks 2, 4, 8, and 10 in the form of the ulcerative colitis disease activity index (score 0-12). Patients undergo endoscopy at Baseline, and Week 8 for assessment of inflammation and pathology using the system defined by Geboes. Other observations will include the number of bowel movements, visible blood in stool, abdominal pain, body temperature, pulse rate, haemoglobin, erythrocyte sedimentation rate (ESR), and serum C reactive protein (CRP) level.

Inclusion Criteria:
1. Age 18 years old or greater.
2. Diagnosis of ulcerative colitis for at least 4 months based on endoscopic appearance or radiographic distribution of disease and corroborated with histopathology (especially the absence of granulomata).
3. Ulcerative colitis DAI greater than or equal to 4 and less than or equal to 9.
4. Active ulcerative colitis that is poorly controlled despite concurrent treatment with oral corticosteroids and/or immunosuppressants as defined:—Stable (±5 mg) corticosteroid dose (prednisone<=20 mg/day or equivalent) for at least 14 days prior to Baseline, or maintenance corticosteroid dose (prednisone<=10 mg/day and <20 mg/day or equivalent) for at least 40 days prior to Baseline—At least a 90 day course of azathioprine or 6-MP prior to Baseline, with a dose of azathioprine<=1.5 mg/kg/day or 6-MP<=1 mg/kg/day (rounded to the nearest available tablet formulation), or a dose that is the highest tolerated by the subject (e.g., due to leukopenia, elevated liver enzymes, nausea) during that time. Subject must be on a stable dose for at least 28 days prior to Baseline Exclusion Criteria
1. History of subtotal colectomy with ileorectostomy or colectomy with ileoanal pouch, Koch pouch, or ileostomy for ulcerative olitis or is planning bowel surgery
2. Received previous treatment with rapamycin or previous participation in an rapamycin clinical study
3. Current diagnosis of fulminant colitis and/or toxic megacolon
4. Subject with disease limited to the rectum (ulcerative proctitis)
5. Current diagnosis of indeterminate colitis
6. Current diagnosis and/or history of Crohn's disease
7. Currently receiving total parenteral nutrition (TPN)

Intervention: Adipose tissue is obtained by liposuction from both placebo and treatment groups, under local anesthesia and general sedation. A hollow blunt-tipped canula is introduced into the subcutaneous space through a small incision (<0.5 cm in diameter). With gentle suction, the canula is moved through the adipose abdominal-wall compartment for mechanical disruption of the fatty tissue. A saline solution and the vasoconstrictor epinephrine are injected into the adipose compartment to minimize blood loss. Using this procedure, 80 to 100 ml of raw of lipoaspirate is obtained from each patient.

The raw lipoaspirate is washed extensively with sterile phosphate-buffered saline (PBS; Gibco BRL, Paisley, Scotland, UK) to remove blood cells, saline, and local anesthetic. The extracellular matrix is digested with a solution of Type II collagenase (0.075 percent; Gibco BRL) in balanced salt solution (5 mg/ml; Sigma, St. Louis, Mo.) for 30 minutes at 37° C. to release the cellular fraction. Then, the collagenase is inactivated by addition of an equal volume of Dulbecco's modified Eagle's medium (DMEM; Gibco BRL), which contained 10 percent fetal bovine serum (FBS; Gibco BRL). The suspension of cells is centrifuged at 250×g for 10 minutes. Cells are resuspended in 0.16 M NH4Cl and allowed to stand for 10 minutes at room temperature (RT) for lysis of erythrocytes. The mixture is then centrifuged at 250×g, and cells are resuspended in DMEM plus 10 percent FBS and 1 percent ampicillin/streptomycin mixture (Gibco, BRL) and then are plated in 100-mm tissue-culture dishes at a concentration of 10 to 15×103 cells/cm2.

G-CSF and FLT-3L are added to the cultures at a concentration of 50 ng/ml in order to activate stem cell function, so in turn to enhance Treg activity.

Cells are cultured for 24 hours at 37° C. in an atmosphere of 5-percent CO2 in air. In contrast to culture of adipose mesenchymal stem cells, in this procedure non-adherent cells are not removed from the culture condition. Cells are subsequently passaged 2 times at a frequency of 3-5 days. During passaging non-adherent cells are gently pipetted off the plate, and adherent cells are trypsinized. Treg cell cells are subsequently purified from the preparation using anti-CD25 MACS beads. A total of approximately 50×106 cells are concentrated in injectable saline with 3% autologous serum and injected intravenously. Patients in the placebo group are injected with saline and 3% autologous serum in order not to bias the patients based on color of the solution being injected.

Outcome: The primary end point of the trial is a positive response as determined by a decrease in the DAI by greater than or equal to 3 points at week 8 that was not accompanied by an increase in dosage of any of the concomitant medications and defined by mucosal healing on endoscopic examination (score of zero on Geboes scaled). Out of 110 patients enrolled, 10 are excluded due to protocol violations. Of 50 patients completing the placebo treatment, the primary end point is reached in 4 patients. Of 50 patients in the treatment group, 45 achieve the primary endpoint.

One skilled in the art will appreciate that these methods, compositions, and cells are and may be adapted to carry out the objects and obtain the ends and advantages mentioned, as well as those inherent therein. The methods, procedures, and devices described herein are presently representative of preferred embodiments and are exemplary and are not intended as limitations on the scope of the invention. Changes therein and other uses will occur to those skilled in the art which are encompassed within the spirit of the invention and are defined by the scope of the disclosure. It will be apparent to one skilled in the art that varying substitutions and modifications may be made to the invention disclosed herein without departing from the scope and spirit of the invention. Those skilled in the art recognize that the aspects and embodiments of the invention set forth herein may be practiced separate from each other or in conjunction with each other. Therefore, combinations of separate embodiments are within the scope of the invention as disclosed herein. All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions indicates the exclusion of equivalents of the features shown and described or portions thereof. It is recognized that various modifications are possible within the scope of the invention disclosed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the disclosure.

The attached file TregSeqListing_ST25.txt contains the Sequence Listing in text format (ASCII) and is hereby expressly incorporated herein by reference in its entirety. TregSeqListing_ST25.txt is 1 KB in size and was created on Dec. 18, 2007.

A) REFERENCES

Each of the following references and all references provided herein are expressly incorporated herein by reference in their entireties.

1. Bjorses, P., et al., *Gene defect behind APECED: a new clue to autoimmunity.* Hum Mol Genet, 1998. 7(10): p. 1547-53.
2. Anderson, M. S., et al., *Projection of an immunological self shadow within the thymus by the aire protein.* Science, 2002. 298(5597): p. 1395-401.
3. Derbinski, J., et al., *Promiscuous gene expression in thymic epithelial cells is regulated at multiple levels.* J Exp Med, 2005. 202(1): p. 33-45.
4. Khoury, S. J., et al., *Mechanisms of acquired thymic tolerance in experimental autoimmune encephalomyelitis: thymic dendritic-enriched cells induce specific peripheral T cell unresponsiveness in vivo.* J Exp Med, 1995. 182(2): p. 357-66.
5. Rastellini, C., et al., *Granulocyte/macrophage colony-stimulating factor-stimulated hepatic dendritic cell progenitors prolong pancreatic islet allograft survival.* Transplantation, 1995. 60(11): p. 1366-70.
6. Thomson, A. W., et al., *Microchimerism, dendritic cell progenitors and transplantation tolerance.* Stem Cells, 1995. 13(6): p. 622-39.
7. Suss, G. and K. Shortman, *A subclass of dendritic cells kills CD4 T cells via Fas/Fas-ligand-induced apoptosis.* J Exp Med, 1996. 183(4): p. 1789-96.
8. Gorczynski, R. M., et al., *Increased expression of the novel molecule OX-2 is involved in prolongation of murine renal allograft survival.* Transplantation, 1998. 65(8): p. 1106-14.
9. Gorczynski, R. M., K. Yu, and D. Clark, *Receptor engagement on cells expressing a ligand for the tolerance-inducing molecule OX2 induces an immunoregulatory population that inhibits alloreactivity in vitro and in vivo.* J Immunol, 2000. 165(9): p. 4854-60.
10. Khanna, A., et al., *Effects of liver-derived dendritic cell progenitors on Th1-and Th2-like cytokine responses in vitro and in vivo.* J Immunol, 2000. 164(3): p. 1346-54.
11. Lutz, M. B., et al., *Immature dendritic cells generated with low doses of GM-CSF in the absence of IL-4 are maturation resistant and prolong allograft survival in vivo.* Eur J Immunol, 2000. 30(7): p. 1813-22.
12. Mahnke, K., et al., *Induction of CD4+/CD25+ regulatory T cells by targeting of antigens to immature dendritic cells.* Blood, 2003. 101(12): p. 4862-9.
13. Min, W. P., et al., *Inhibitory feedback loop between tolerogenic dendritic cells and regulatory T cells in transplant tolerance.* J Immunol, 2003. 170(3): p. 1304-12.
14. Ichim, T. E., R. Zhong, and W. P. Min, *Prevention of allograft rejection by in vitro generated tolerogenic dendritic cells.* Transpl Immunol, 2003. 11(3-4): p. 295-306.
15. Fukuma, K., et al., *Immunologic and clinical studies on murine experimental autoimmune gastritis induced by neonatal thymectomy.* Gastroenterology, 1988. 94(2): p. 274-83.
16. Sakaguchi, S. and N. Sakaguchi, *Organ-specific autoimmune disease induced in mice by elimination of T cell subsets. V. Neonatal administration of cyclosporin A causes autoimmune disease.* J Immunol, 1989. 142(2): p. 471-80.
17. Loughry, A., et al., *Inflammatory arthritis and dermatitis in thymectomized, CD25+ cell-depleted adult mice.* Rheumatology (Oxford), 2005. 44(3): p. 299-308.
18. Kohm, A. P., P. A. Carpentier, and S. D. Miller, *Regulation of experimental autoimmune encephalomyelitis (EAE) by CD4+CD25+ regulatory T cells.* Novartis Found Symp, 2003. 252: p. 45-52; discussion 52-4, 106-14.
19. Veltkamp, C., et al., *CD4+CD25+ cell depletion from the normal CD4+ T cell pool prevents tolerance toward the intestinal flora and leads to chronic colitis in immunodeficient mice.* Inflamm Bowel Dis, 2006. 12(6): p. 437-46.
20. Zhang, L., et al., *Transforming growth factor-beta: an important role in CD4+CD25+ regulatory T cells and immune tolerance.* Autoimmunity, 2006. 39(4): p. 269-76.
21. Fallarino, F., et al., *Modulation of tryptophan catabolism by regulatory T cells.* Nat Immunol, 2003. 4(12): p. 1206-12.
22. Jarnicki, A. G., et al., *Suppression of antitumor immunity by IL-10 and TGF-beta-producing T cells infiltrating the growing tumor: influence of tumor environment on the induction of CD4+ and CD8+ regulatory T cells.* J Immunol, 2006. 177(2): p. 896-904.
23. Sakaguchi, S., et al., *Foxp3+ CD25+ CD4+ natural regulatory T cells in dominant self-tolerance and autoimmune disease.* Immunol Rev, 2006. 212: p. 8-27.

24. Curiel, T. J., et al., *Specific recruitment of regulatory T cells in ovarian carcinoma fosters immune privilege and predicts reduced survival*. Nat Med, 2004. 10(9): p. 942-9.
25. Lee, A. M., et al., *Number of CD4+ cells and location of forkhead box protein P3-positive cells in diagnostic follicular lymphoma tissue microarrays correlates with outcome*. J Clin Oncol, 2006. 24(31): p. 5052-9.
26. Hegmans, J. P., et al., *Mesothelioma environment comprises cytokines and T-regulatory cells that suppress immune responses*. Eur Respir J, 2006. 27(6): p. 1086-95.
27. Dannull, J., et al., *Enhancement of vaccine-mediated anti-tumor immunity in cancer patients after depletion of regulatory T cells*. J Clin Invest, 2005. 115(12): p. 3623-33.
28. Maker, A. V., et al., *Tumor regression and autoimmunity in patients treated with cytotoxic T lymphocyte-associated antigen 4 blockade and interleukin 2: a phase I/II study*. Ann Surg Oncol, 2005. 12(12): p. 1005-16.
29. Maker, A. V., et al., *Intrapatient dose escalation of anti-CTLA-4 antibody in patients with metastatic melanoma*. J Immunother, 2006. 29(4): p. 455-63.
30. Phan, G. Q., et al., *Cancer regression and autoimmunity induced by cytotoxic T lymphocyte-associated antigen 4 blockade in patients with metastatic melanoma*. Proc Natl Acad Sci USA, 2003. 100(14): p. 8372-7.
31. Toubi, E., et al., *Increased spontaneous apoptosis of CD4+CD25+ T cells in patients with active rheumatoid arthritis is reduced by infliximab*. Ann NY Acad Sci, 2005. 1051: p. 506-14.
32. Sanchez-Ramon, S., et al., *Pregnancy-induced expansion of regulatory T-lymphocytes may mediate protection to multiple sclerosis activity*. Immunol Lett, 2005. 96(2): p. 195-201.
33. Takahashi, M., et al., *An inverse correlation of human peripheral blood regulatory T cell frequency with the disease activity of ulcerative colitis*. Dig Dis Sci, 2006. 51(4): p. 677-86.
34. Wing, K., et al., *Characterization of human CD25+ CD4+ T cells in thymus, cord and adult blood*. Immunology, 2002. 106(2): p. 190-9.
35. Betre, H., et al., *Chondrocytic differentiation of human adipose-derived adult stem cells in elastin-like polypeptide*. Biomaterials, 2006. 27(1): p. 91-9.
36. Wei, Y., et al., *Regulation of adipose-derived adult stem cells differentiating into chondrocytes with the use of rhBMP-2*. Cytotherapy, 2006. 8(6): p. 570-9.
37. Jeon, E. S., et al., *Sphingosylphosphorylcholine induces differentiation of human mesenchymal stem cells into smooth-muscle-like cells through a TGF-[beta]-dependent mechanism*. J Cell Sci, 2006. 119(Pt 23): p. 4994-5005.
38. Rodriguez, L. V., et al., *Clonogenic multipotent stem cells in human adipose tissue differentiate into functional smooth muscle cells*. Proc Natl Acad Sci USA, 2006. 103(32): p. 12167-72.
39. Kim, M., et al., *Muscle regeneration by adipose tissue-derived adult stem cells attached to injectable PLGA spheres*. Biochem Biophys Res Commun, 2006. 348(2): p. 386-92.
40. Di Rocco, G., et al., *Myogenic potential of adipose-tissue-derived cells*. J Cell Sci, 2006. 119(Pt 14): p. 2945-52.
41. Talens-Visconti, R., et al., *Human mesenchymal stem cells from adipose tissue: Differentiation into hepatic lineage*. Toxicol In Vitro, 2006.
42. Talens-Visconti, R., et al., *Hepatogenic differentiation of human mesenchymal stem cells from adipose tissue in comparison with bone marrow mesenchymal stem cells*. World J Gastroenterol, 2006. 12(36): p. 5834-45.
43. Seo, M. J., et al., *Differentiation of human adipose stromal cells into hepatic lineage in vitro and in vivo*. Biochem Biophys Res Commun, 2005. 328(1): p. 258-64.
44. Cao, Y., et al., *Human adipose tissue-derived stem cells differentiate into endothelial cells in vitro and improve postnatal neovascularization in vivo*. Biochem Biophys Res Commun, 2005. 332(2): p. 370-9.
45. Planat-Benard, V., et al., *Spontaneous cardiomyocyte differentiation from adipose tissue stroma cells*. Circ Res, 2004. 94(2): p. 223-9.
46. Barrilleaux, B., et al., *Review: Ex Vivo Engineering of Living Tissues with Adult Stem Cells*. Tissue Eng, 2006.
47. Zenclussen, A. C., *Regulatory T cells in pregnancy*. Springer Semin Immunopathol, 2006. 28(1): p. 31-9.
48. Frey, O. and R. Brauer, *Regulatory T cells: magic bullets for immunotherapy?* Arch Immunol Ther Exp (Warsz), 2006. 54(1): p. 33-43.
49. Fritzsching, B., et al., *Naive regulatory T cells: a novel subpopulation defined by resistance towards CD95L-mediated cell death*. Blood, 2006.
50. Godfrey, W. R., et al., *Cord blood CD4(+)CD25(+)-derived T regulatory cell lines express FoxP3 protein and manifest potent suppressor function*. Blood, 2005. 105(2): p. 750-8.
51. Takahata, Y., et al., *CD25+CD4+ T cells in human cord blood: an immunoregulatory subset with naive phenotype and specific expression of forkhead box p3 (Foxp3) gene*. Exp Hematol, 2004. 32(7): p. 622-9.
52. Sakaguchi, S., et al., *Foxp3CD25CD4 natural regulatory T cells in dominant self-tolerance and autoimmune disease*. Immunol Rev, 2006. 212: p. 8-27.
53. Torgerson, T. R., *Regulatory T cells in human autoimmune diseases*. Springer Semin Immunopathol, 2006. 28(1): p. 63-76.

What is claimed is:

1. A method of immune modulation in a patient comprising the steps of:
   a) selecting a patient in need of immune modulation; and
   b) administering a therapeutically effective amount of adipose derived mononuclear T regulatory cells having enhanced immune modulatory activity compared to said mononuclear cells in a substantially unpurified state.

2. The method of claim 1, wherein said adipose derived mononuclear cells are autologous such that they are derived from the patient in need.

3. The method of claim 1, wherein said adipose derived mononuclear cells are subjected to a culturing step, said culturing step comprising of exposure to an agent or plurality of agents capable of augmenting immune regulatory ability of said adipose derived mononuclear cells.

4. The method of claim 1, wherein a compound or plurality of compounds are administered prior to, concurrently with, or subsequently to administration of said adipose derived mononuclear cells in order to augment immune regulatory activity.

5. The method of claim 1, wherein said adipose derived mononuclear cells are autologous and have a higher immune modulatory activity compared to autologous mononuclear cells derived from peripheral blood.

6. A method of immune modulation comprising administration of autologous mononuclear T regulatory cells isolated from adipose tissue into a patient, said cells administered in combination with an agent capable of suppressing TNF-alpha activity.

7. A method of immune modulation comprising: a) extracting a heterogeneous population of adipose derived cells containing a T regulatory and stem cell population therein; b) treating said heterogeneous population with one or more activators of stem cell proliferation; c) treating said heterogeneous population with one or more agents capable of enhancing Treg activation/expansion; and d) administering said heterogeneous population into a patient.

8. A method of immune modulation comprising: a) extracting a heterogeneous population of adipose derived cells containing a T regulatory and stem cell population therein; b) treating said heterogeneous population with one or more activators of stem cell proliferation; c) treating said heterogeneous population with one or more agents capable of enhancing Treg activation/expansion; and d) purifying said Treg populations and/or stem cell populations and administering into a patient depending on immune modulation desired.

* * * * *

UNITED STATES PATENT AND TRADEMARK OFFICE
Certificate

Patent No. 8,241,621 B2                                                                                                                              Patented: August 14, 2012

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Thomas E. Ichim, San Diego, CA (US); and Neil H. Riordan, Trophy Club, TX (US).

Signed and Sealed this Twentieth Day of May 2014.

*JOANNE HAMA*
*Supervisory Patent Examiner*
*Art Unit 1647*
*Technology Center 1600*